(12) United States Patent
Overes et al.

(10) Patent No.: US 9,675,466 B2
(45) Date of Patent: Jun. 13, 2017

(54) EXPANDABLE SPINAL IMPLANT

(71) Applicant: 41medical AG, Bettlach (CH)

(72) Inventors: Tom Overes, Langendorf (CH); Robert Frigg, Bettlach (CH)

(*) Notice: Subject to any disclaimer, the term of this patent is extended or adjusted under 35 U.S.C. 154(b) by 0 days.

(21) Appl. No.: 15/034,163

(22) PCT Filed: Aug. 18, 2014

(86) PCT No.: PCT/CH2014/000122
§ 371 (c)(1),
(2) Date: May 3, 2016

(87) PCT Pub. No.: WO2015/066823
PCT Pub. Date: May 14, 2015

(65) Prior Publication Data
US 2016/0278935 A1 Sep. 29, 2016

(30) Foreign Application Priority Data

Nov. 11, 2013 (CH) ...................... 1883/13

(51) Int. Cl.
*A61F 2/44* (2006.01)
*A61F 2/30* (2006.01)
*A61F 2/46* (2006.01)

(52) U.S. Cl.
CPC ............ *A61F 2/4425* (2013.01); *A61F 2/442* (2013.01); *A61F 2/447* (2013.01); *A61F 2/4455* (2013.01); *A61F 2002/3054* (2013.01); *A61F 2002/30179* (2013.01); *A61F 2002/30471* (2013.01); *A61F 2002/30523* (2013.01); *A61F 2002/30525* (2013.01); *A61F 2002/30579* (2013.01); *A61F 2002/4485* (2013.01); *A61F 2002/4629* (2013.01); *A61F 2310/00023* (2013.01)

(58) Field of Classification Search
CPC .. A61F 2/44; A61F 2/4425; A61F 2/30; A61F 2/46
See application file for complete search history.

(56) References Cited

U.S. PATENT DOCUMENTS

| | | | | |
|---|---|---|---|---|
| 5,390,683 A * | 2/1995 | Pisharodi | ............... | A61F 2/442 128/898 |
| 6,126,689 A * | 10/2000 | Brett | .................... | A61F 2/4455 623/17.15 |
| 7,087,055 B2 * | 8/2006 | Lim | .................... | A61B 17/025 606/198 |
| 2004/0059271 A1 * | 3/2004 | Berry | ....................... | A61F 2/44 602/32 |

(Continued)

FOREIGN PATENT DOCUMENTS

WO 2009/098536 A1 8/2009
WO 2011/141869 A1 11/2011

*Primary Examiner* — Ellen C Hammond
*Assistant Examiner* — Stuart S Bray
(74) *Attorney, Agent, or Firm* — Garrett James O'Sullivan (57) ABSTRACT

The present application relates to an expandable spinal implant comprising three or more elongated implant members. The implant members are rotatably coupled to a central base portion and comprise a first end with an axis of rotation and circumferentially arranged gear teeth. The gear teeth of at least one of said elongated implant members are interlocked into said gear teeth of the two other elongated implant members.

11 Claims, 6 Drawing Sheets

(56) References Cited

U.S. PATENT DOCUMENTS

| | | | |
|---|---|---|---|
| 2004/0153156 A1* | 8/2004 | Cohen | A61F 2/44 623/17.13 |
| 2005/0021144 A1 | 1/2005 | Malberg et al. | |
| 2005/0113920 A1* | 5/2005 | Foley | A61F 2/4455 623/17.11 |
| 2005/0131536 A1* | 6/2005 | Eisermann | A61F 2/447 623/17.11 |
| 2006/0095136 A1* | 5/2006 | McLuen | A61F 2/4455 623/23.47 |
| 2006/0142858 A1* | 6/2006 | Colleran | A61F 2/4465 623/17.11 |
| 2006/0195089 A1 | 8/2006 | LeHuec et al. | |
| 2006/0224241 A1* | 10/2006 | Butler | A61B 17/8858 623/17.15 |
| 2007/0225808 A1 | 9/2007 | Warnick | |
| 2008/0071376 A1* | 3/2008 | Kohm | A61B 17/025 623/17.16 |
| 2008/0177391 A1* | 7/2008 | Mitchell | A61B 17/7065 623/17.16 |
| 2008/0212405 A1* | 9/2008 | Globerman | B01F 7/005 366/288 |
| 2008/0243254 A1* | 10/2008 | Butler | A61F 2/44 623/17.16 |
| 2008/0312741 A1* | 12/2008 | Lee | A61B 17/7068 623/17.11 |
| 2009/0048676 A1 | 2/2009 | Fabian, Jr. | |
| 2010/0185291 A1* | 7/2010 | Jimenez | F16C 11/12 623/17.16 |
| 2010/0222816 A1 | 9/2010 | Gabelberger et al. | |
| 2011/0208306 A1* | 8/2011 | Farris | A61F 2/442 623/17.11 |
| 2011/0218631 A1* | 9/2011 | Woodburn, Sr. | A61F 2/442 623/17.16 |
| 2012/0029639 A1 | 2/2012 | Blackwell et al. | |
| 2012/0150229 A1* | 6/2012 | Hess | A61B 17/7065 606/249 |
| 2012/0197299 A1 | 8/2012 | Fabian, Jr. | |
| 2012/0197403 A1* | 8/2012 | Merves | A61F 2/44 623/17.16 |
| 2012/0232659 A1* | 9/2012 | Himmelberger | A61F 2/44 623/17.16 |
| 2013/0079883 A1* | 3/2013 | Butler | A61F 2/4425 623/17.16 |
| 2013/0103156 A1* | 4/2013 | Packer | A61F 2/442 623/17.16 |
| 2013/0110239 A1* | 5/2013 | Siegal | A61B 17/7098 623/17.16 |
| 2013/0158668 A1* | 6/2013 | Nichols | A61F 2/4611 623/17.16 |
| 2014/0107787 A1* | 4/2014 | Stinchfield | A61F 2/44 623/17.16 |
| 2014/0207236 A1* | 7/2014 | Prevost | A61F 2/44 623/17.16 |
| 2014/0288652 A1* | 9/2014 | Boehm | A61F 2/4465 623/17.15 |
| 2014/0343678 A1* | 11/2014 | Suddaby | A61F 2/46 623/17.16 |
| 2015/0018957 A1* | 1/2015 | Nichols | A61F 2/4611 623/17.16 |
| 2015/0025634 A1* | 1/2015 | Boehm | A61F 2/4425 623/17.15 |
| 2015/0066146 A1* | 3/2015 | Laubert | A61F 2/442 623/17.16 |
| 2015/0148908 A1* | 5/2015 | Marino | A61F 2/4455 623/17.16 |
| 2015/0313585 A1* | 11/2015 | Abidin | A61B 17/0206 600/213 |
| 2016/0081811 A1* | 3/2016 | McKay | A61F 2/44 623/17.13 |
| 2016/0278933 A1* | 9/2016 | Semler | A61F 2/442 |

\* cited by examiner

EXPANDABLE SPINAL IMPLANT

TECHNICAL FIELD

The invention relates to an expandable spinal implant to be arranged between two adjacent vertebral bodies.

BACKGROUND ART

Low back pain is a common disease for example caused by herniated discs, compressed nerve roots, degenerative discs or joint disease.

If a patient has this severe pain and does not respond to conservative treatment, spinal fusion is an option to eliminate the pain. Spinal fusion is a surgical technique, wherein two or more vertebrae are joined together. Spinal fusion interventions are also performed to correct back deformities.

With inter-body fusion often an intervertebral spacer or device is placed between the involved vertebrae after removal of the intervertebral disc. The intervertebral device corrects the spine alignment and restores the disc height.

Common intervertebral devices are made from titanium alloys or polyetheretherketone (PEEK). Often these devices comprise pockets that can be filled with bone graft material or artificial graft substitute. The fusion itself takes place when the bone of the endplates grows into and through the intervertebral device. Finally both vertebrae are grown together. Often, additionally, a pedicle system provides additional posterior stabilisation. Intervertebral fusion devices can be implanted with various approaches, for example from the anterior, the posterior or the lateral side.

Over the past years minimal invasive techniques have been introduced. The advantages of the minimal invasive techniques are less soft tissue trauma resulting in a faster recovery. Other complications are reduced as well. In minimal invasive techniques the implant is brought into position between the vertebrae through a small incision with small instruments. Still the intervertebral device must have a sufficient large foot-print to translate the forces between the vertebrae before complete fusion has taken place. If a device is too small, it will sink into or break through the endplate of the vertebra, and the initially restored height is lost.

Combining advantages of the minimal invasive surgery approaches with well supporting intervertebral devices with large foot-print, a device would be required that can be brought into place through a small incision, and in a second step is expanded to a larger size.

Various embodiments of such devices are known in the art. For example, WO 2009/098536 (Calvosa Giuseppe) discloses an intervertebral distractor comprising stop members and which may be percutaneously implanted. The distractor comprises an elongated body adapted to provide an interspinous support between two adjacent spinous processes as well as a first and a second couple of mobile stabilizers which are adapted to rotate from a closed position to a spread apart position. Further, the distractor includes means for bringing said stabilizers from the closed position into the spread apart position, wherein said means are movable along a longitudinal axis of said distractor and being coupled to one end of each of said stabilizers to rotate said stabilizers from said closed position to said spread apart position.

US 2009/0048676 A1 (Henry Fabian JR) describes an implant comprising two members being pivotal relative to each other and each comprising two limbs. The implant may be inserted into a vertebral space in a first non-expanded configuration, where all limbs are adjacent to each other, and which may then subsequently be deployed to a second expanded configuration having a larger foot-print, where the limbs are separated from each other. The implant may further comprise a locking mechanism used to lock the position of the first member relative to the second member. Deployment of the implant from the first configuration to the second configuration is performed by a cable which may be pulled by a surgeon such as to expand the implant.

US 2012/0029639 discloses interbody spinal implants being implantable into a patient in a first orientation having a reduced height and then rotated to a second orientation which extends the height of the implant.

The implants known in the art have the disadvantage that the expansion of the different implant parts may not be equal due to different forces acting on each part. For example, the use of a cable exerts a maximal force onto one part which is directly coupled to the cable, while the force exerted on other parts may be diminished by external forces acting on these parts.

SUMMARY OF THE INVENTION

It is the object of the invention to create an expandable spinal implant that allows a uniform movement of any part of the implant, thus yielding a uniform deployment of the implant in the intervertebral space between adjacent vertebrae.

The solution of the invention is specified by the features of claim 1. According to the invention the expandable spinal implant comprises three or more elongated implant members. Each of said implant members is rotatably coupled to a central base portion and comprises a first end with an axis of rotation and circumferentially arranged gear teeth. The gear teeth of at least one of said implant members are interlocked into said gear teeth of the two other implant members.

By rotating one single elongated implant member around its axis of rotation, the at least two other elongated implant members are also moved around their respective axes of rotation. The transmission of the rotation movement by means of a gear tooth system ensures a uniform transmission of the rotation movement and hence allows a uniform deployment of all the elongated implant members.

The expandable spinal implant according to the present invention is expandable in a plane which is essentially parallel to the surfaces of the vertebral bodies facing towards the intervertebral space the expandable spinal implant is to be implanted into. Hence, expansion of the inventive expandable spinal implant only results in an expansion of the overall foot-print of the expandable spinal implant while the distance between the adjacent vertebrae is not increased.

The interlocking of the gear teeth of the at least one elongated implant member with the gear teeth of the two other elongated implant members results in a kind of gear system, wherein upon rotation of the at least one elongated implant member in one direction, the two other elongated implant members are rotatably moved into an opposite direction.

Preferably, all the elongated implant members have gear teeth which are arranged at the same distance from the axis of rotation, i.e. the gear ratio between any of the elongated implant members is 1:1. Hence, rotation of said at least one elongated implant member by a specific angle will provoke a rotation of the other elongated implant members by the same angle.

Alternatively, the distance between the teeth to the axis of rotation of at least one of the elongated implant members may be chosen to be unequal to the distance of the other elongated implant members. This results in different rotational speeds of the elongated implant members, i.e. to a gear ratio which is higher or lower than 1:1.

Provision of gear teeth for each elongated implant member interlocking with each other allows the expansion of the expandable spinal implant by exerting a pulling force on any of the elongated implant members, as rotation of any of said elongated implant members will exert a rotational force onto all the other elongated implant members.

The axes of rotation of each of the elongated implant members are preferably parallel to each other. The gear teeth are arranged around said axes along at least a portion of a circle. Preferably, the gear teeth are arranged around a half circle or a quadrant of a circle, said circle having its centre located on the axis of rotation of the respective elongated implant member.

The elongated implant members preferably have a base area which is in the form of a trapezoid, more preferably of a right angle trapezoid. Further preferably, at least one corner area of each of said elongated implant members is rounded such as to ease the insertion of the expandable spinal implant without causing any irritation to the annulus. The circumferentially arranged gear teeth are preferably located on one of the smaller sides of the elongated implant members.

The elongated implant members each preferably have a lower surface and an upper surface configured to contact bone of two adjacent vertebral bodies. Said lower and said upper surface are spaced from each other by a thickness which preferably corresponds to the natural height of an intervertebral disc. Both surfaces may be arranged parallel to each other, however preferably, the thickness of the elongated implant members varies from one end of the expandable spinal implant which is to be arranged on a ventral side of the intervertebral space to the side which is to be arranged on a dorsal side of the intervertebral space. This allows conforming the shape of the expandable spinal implant to the natural shape of the intervertebral space.

Said upper surface and said lower surface preferably include a structure which enhances the friction between the surfaces and the bone of the adjacent vertebral bodies. Said structure may e.g. comprise a multitude of ribs, burls, pyramid shape protrusions or the like. Such a structure enhances the friction between the elongated implant members and the vertebral bone, hence safely anchoring the expandable spinal implant in the intervertebral space.

The central base portion constitutes the attachment point of all elongated implant members. Hence, each elongated implant member is rotatably coupled to said central base portion by means of its rotation axis. The central base portion is preferably in the form of a plate. Preferably, said central base portion has a polygonal base area with a number of corners which corresponds to the number of elongated implant members. E.g. if the expandable spinal implant comprises three elongated implant members, the central base portion will be in the form of a triangle, whereas if the expandable spinal implant comprises five elongated implant members, the central base portion will be in the form of a pentagon.

Preferably, said three or more elongated implant members each include a recess into which a corner of the central base portion may be inserted. This allows configuring the expandable spinal implant with flush surfaces. More preferably, said recess is arranged centrally between the upper surface and the lower surface of each of said elongated implant members. This allows to insert the corners of the central base portion into said recesses and to rotatably couple the central base portion on both sides with each of said elongated implant members by means of a peg or pin, hence increasing the stability of the coupling between the central base plate and each of the elongated implant members. Preferably, circumferentially arranged gear teeth are arranged on both sides of said recess.

Preferably, the expandable spinal implant is made of titanium or a titanium alloy. Further preferably, the expandable spinal implant may be made of a biocompatible polymer, most preferably of polyetheretherketone (PEEK) or of fiber reinforced polyetheretherketone. Further, the expandable spinal implant may be made of a combination of materials.

Preferably, the elongated implant members are substantially parallel in an initial and unexpanded configuration. This allows minimizing the size of the expandable spinal implant for implantation, hence allowing the insertion of the expandable spinal implant through an incision with small dimensions.

Preferably, the expandable spinal implant comprises four elongated implant members, wherein said four elongated implant members from a substantially X-shaped footprint in an expanded configuration. Provision of the expandable spinal implant in the shape of an X provides a large foot-print of the expandable spinal implant once expanded, hence allowing a good distribution of the loads transmitted between the adjacent vertebrae via said expandable spinal implant.

In alternative, preferred embodiment, the expandable spinal implant comprises three elongated implant members, wherein said three elongated implant members from a substantially Y-shaped footprint in an expanded configuration. This shape may be more suited in certain specific applications. Further, a Y-shaped implant allows an even distribution of the loads transmitted between the adjacent vertebrae via said expandable spinal implant. A person having skill in the art will recognize that only one elongated implant member will cooperate with the two other elongated implant members, as otherwise no expansion would be possible.

The expandable spinal implant preferably comprises at least one pocket for receiving bone graft material. Preferably said at least one pocket is arranged in one of the elongated implant members and spans the entire thickness of said elongated implant member, i.e. the pocket is in the form of a bore or hole spanning the entire thickness of said elongated implant member. Provision of such a pocket allows applying bone graft material linking both vertebrae together. This enhances the ingrowth of bone through the expandable spinal implant. Preferably, each of said elongated implant members comprises at least one pocket for receiving bone ingrowth material.

Preferably, said expandable spinal implant comprises elongated implant members of unequal length. This allows tailoring the expandable spinal implant to different intervertebral spaces, e.g. depending on the type of vertebrae adjacent said intervertebral space. For example, the configuration of the lengths of the elongated implant members may be different if the expandable spinal implant is to be implanted between thoracic vertebrae or between lumbar vertebrae.

The expandable spinal implant preferably comprises a worm arranged in said central base portion, said worm engaging a second set of gear teeth arranged on one of said elongated implant members.

Hence, a worm-gear type drive of the expandable spinal implant may be realized. The worm preferably includes a drive to be connected with an appropriate instrument, thus enabling the expansion of the expandable spinal implant by a surgeon by the use of the instrument.

Preferably, the worm is of the self-locking type. This secures the elongated implant members from any movement towards the initial and unexpanded configuration due to forces exerted on any of said elongated implant members. However, further expansion or collapse of the expandable spinal implant by means of the instrument remains possible.

Preferably, the worm is arranged in a channel provided in said central base portion, said channel having an opening allowing the insertion of the instrument by a surgeon.

In an alternatively preferred embodiment, the expandable spinal implant comprises a dowel having a first structure on one end, said first structure cooperating with a second structure on at least one of said elongated implant elements in a form-fitting manner, such as to rotate said one elongated implant member relative to said central base structure.

Preferably, said dowel is cylindrical and comprises as first structure two ring-like enlargements at said one end, wherein said two ring-like enlargements are separated from each other by a distance. Correspondingly, the at least one of said elongated implant elements comprises as second structure two recesses preferably provided on a circular section. Both recesses are spaced apart by a length which corresponds to the distance separating the two ring-like enlargements. This provides a simple and easy to use drive for the expandable spinal implant, as a linear movement of the dowel will exert a pulling or pushing force on said elongated implant member, resulting in a rotational movement of said elongated implant member.

Alternatively, the dowel may comprise a single protrusion which engages into a single groove provided on said one elongated implant member.

However, as a person having skill in the art will easily recognize the recess(es) as mentioned above may also be provided on said dowel while the ring-like enlargements or the protrusion may be located on said elongated implant member.

Further, any suitable type of form-fit interaction may be used for cooperation of said dowel with the elongated implant member.

A person having skill in the art will recognize that the elongated implant member cooperating with said worm or said dowel as explained above preferably is the at least one elongated implant member which has its gear teeth interlocked with the gear teeth of the at least two other elongated implant members.

Preferably, the dowel is arranged in a channel provided in said central base portion, said channel having an opening allowing the insertion of the instrument by a surgeon, such as to push or pull the dowel to move it relative to said central base portion.

Preferably, said dowel comprises a drive at a second end arranged opposite of said first end, such that an instrument to move said dowel may be inserted into said drive. More preferably, an outer thread is arranged on said second end, said outer thread cooperating with a matching inner thread provided in said central base portion of the expandable spinal implant, preferably in said bore or channel. Hence, by imparting a turning motion to said dowel, the dowel will be linearly moved relative to said central base portion, thus imparting a pulling or pushing force onto said elongated implant member by means of the form-fit interaction of the two structures.

Preferably, each of the at least three elongated implant members comprises a lower surface and an upper surface, said two surfaces being arranged at an angle to each other. Said angle more preferably is from 5° to 15°.

The two surfaces are located on the two sides of the elongated implant members intended to be in contact with the bone of adjacent vertebrae. By varying the angle of the upper and lower surfaces relative to each other allows to restore the natural lordotic or kyphotic curvature of the spine.

The present application further relates to a kit comprising multiple expandable spinal implants according to the present invention, wherein the implants have incremental thicknesses between 8 and 20 mm. Hence, a surgeon may always select the expandable spinal implant having an appropriate thickness for the intervertebral space to be treated. Further preferably, the kit may also comprise multiple expandable spinal implants according to the present invention having different combinations of elongated implant member lengths and/or elongated implant member widths.

Preferably, the kit comprises expandable spinal implants having varying angles between a lower surface and an upper surface of the elongated implant members. This allows a surgeon to select an implant which has an optimal angle to restore the natural lordotic or kyphotic curvature of a patient's spine.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
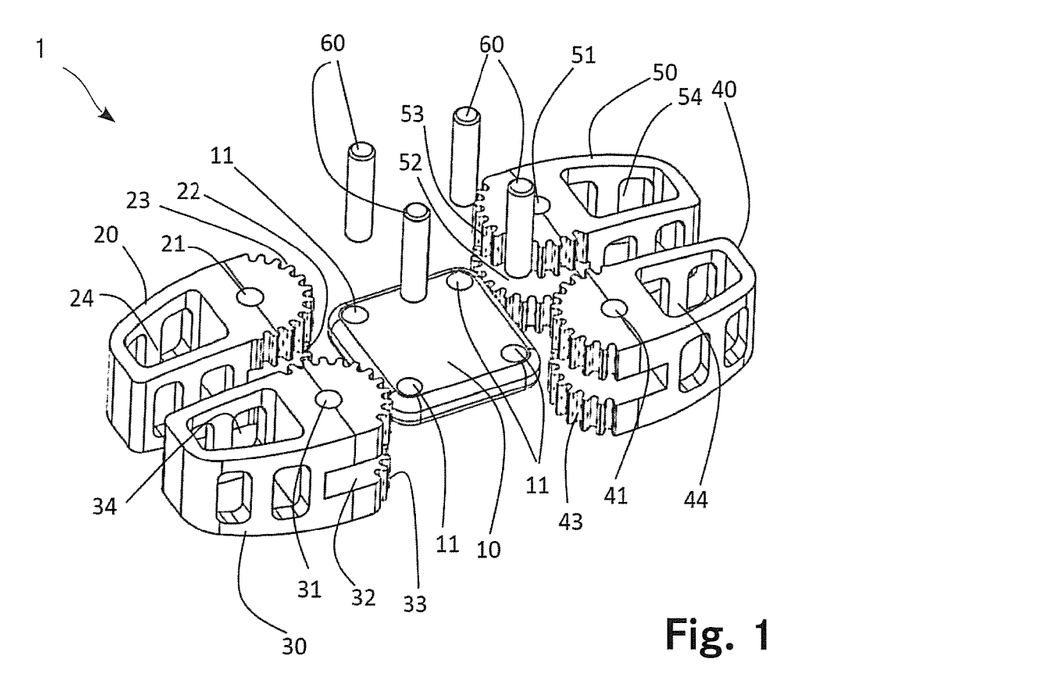
FIG. 1 a first embodiment of an expandable spinal implant according to the present invention in an exploded view.

FIG. 1 shows a first embodiment of the expandable spinal implant 1 in an exploded view. The expandable spinal implant 1 comprises four implant members 20, 30, 40, 50, a central base portion 10 and four hinge-pins 60.

Each of the elongated implant members 20, 30, 40, 50 comprises an axis of rotation at a first end. Each axis of rotation is defined by a corresponding bore 21, 31, 41, 51 into which one of the four hinge-pins 60 may be inserted. Furthermore, the elongated implant members 20, 30, 40, 50 each comprise a recess 22, 32, 42, 52 extending through the elongated implant member 20, 30, 40, 50 and intersecting with the bores 21, 31, 41, 51, wherein each recess 22, 32, 42, 52 is substantially perpendicularly arranged in reference to the respective axis of rotation defined by each bore 21, 31, 41, 51. At said first end the elongated implant members 20, 30, 40, 50 are of a half cylindrical shape, and comprise a set of gear teeth 23, 33, 43, 53, circumferentially arranged around the axis of rotation defined by bores 21, 31, 41, 51. The gear teeth 23, 33, 43, 53 are arranged on both sides of the recesses 22, 32, 42, 52. Towards a second end, the elongated implant members 20, 30, 40, 50 each comprise a pocket 24, 34, 44, 54 extending from the top surface to the bottom surface, wherein the pockets 24, 34, 44, 54 are shaped to receive bone graft material or a bone graft substitute, to promote bone ingrowth.

The central base portion 10 is a block shaped element comprising four substantially parallel through-bores 11, extending form the top side and to the bottom side of the central base portion 10. Said through bores 10 are configured to each receive one of the four hinge-pins 60 such as to rotatably couple each of the elongated implant members 20, 30, 40, 50 to said central base portion.

Figure 2:
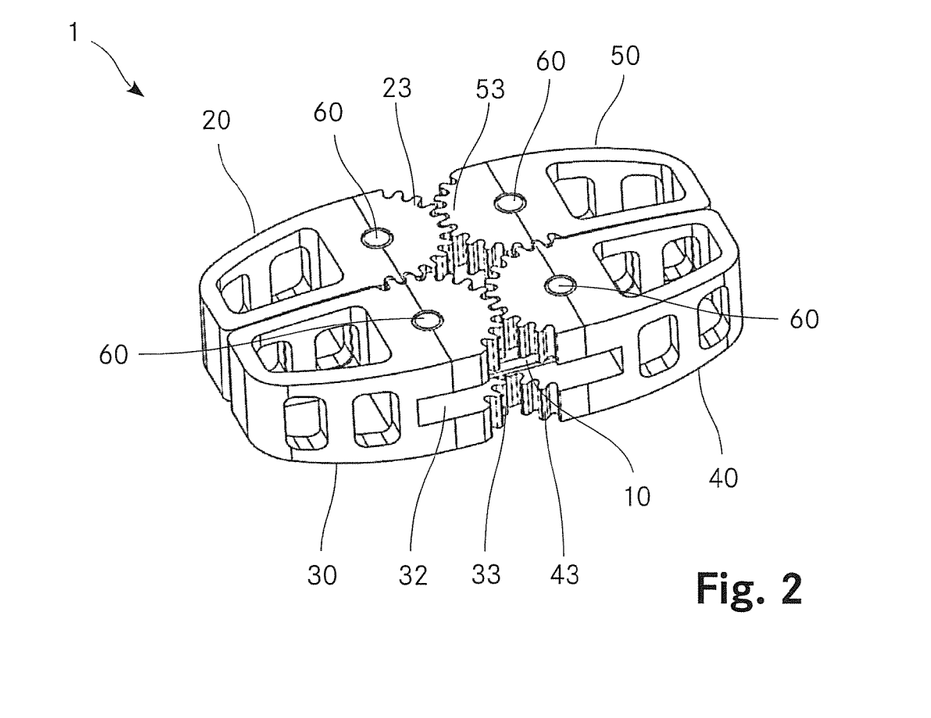
FIG. 2 the expandable spinal implant according to FIG. 1 in an assembled configuration.

FIG. 2 shows the expandable spinal implant 1 in assembled configuration. All four elongated implant members 20, 30, 40, 50 are rotatably coupled to the central base portion 10 by means of four hinge-pins 60 which are introduced into the bores 21, 31, 41, 51 of the elongated implant members 20, 30, 40, 50 and through the through bores 11 of the central base portion 10. The central base portion 10 is arranged within the recesses 22, 32, 42, 52 of the elongated implant members 20, 30, 40, 50. All elongated implant members 20, 30, 40, 50 may only rotate around their hinge axis 21, 31, 41, 51. The sets of teeth 23, 33, 43, 53 all are interlocked, wherein each seat of gear teeth 23, 33, 43, 53 is interlocked into two adjacent sets of gear teeth 23, 33, 43, 53. For example, the first gear teeth 23 of the first elongated implant member 20 are engaged with the second gear teeth 33 of the second elongated implant member 30. These second gear teeth 33 are themselves further engaged with the third gear teeth 43 of the third elongated implant member 40. Said third gear teeth 43 are themselves engaged with the fourth gear teeth 53 of the fourth elongated implant member 50. Finally, said fourth gear teeth 43 are engaged with the first gear teeth 23. As a result, upon actuation or rotation of any of the elongated implant members 20, 30, 40, 50, all the other implant members 20, 30, 40, 50 will be actuated or rotated.

Figure 3A:
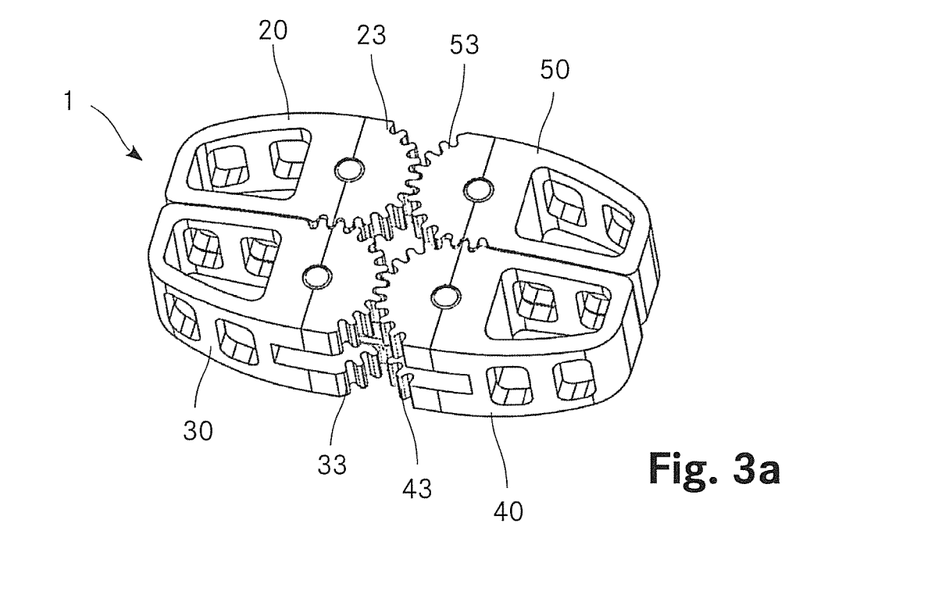
FIG. 3a, 3b the expansion of the expandable spinal implant according to FIG. 1.
Figure 3B:
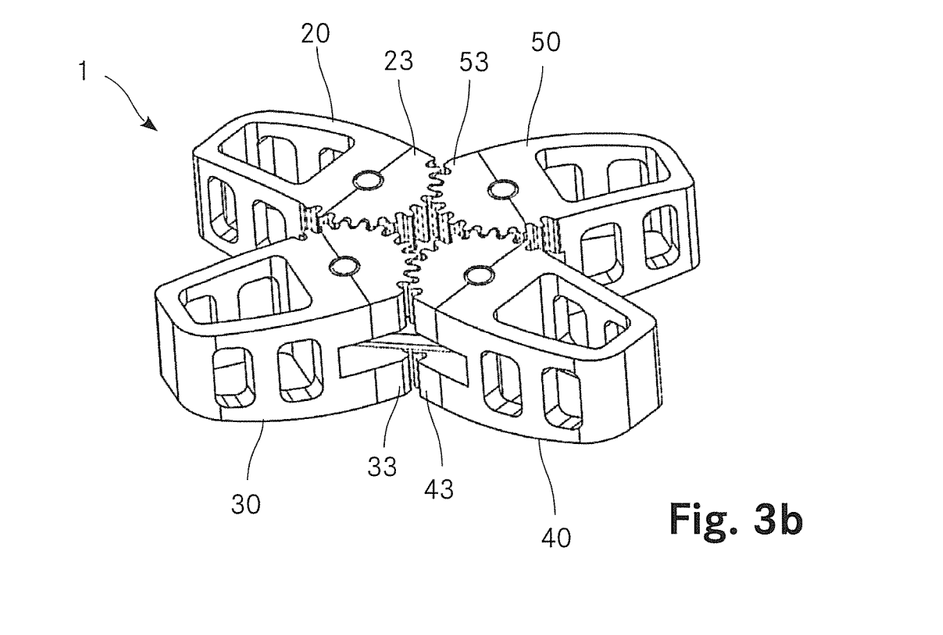

FIGS. 3a and 3b show the expansion of the expandable spinal implant 1 according to FIG. 2. In a first initial and un-expanded configuration, the elongated implant members 20, 30, 40, 50 are pairwise oriented parallel to each other. The expandable spinal implant 1 has a substantially rectangular and narrow footprint in said first initial configuration, as shown in FIG. 3a. Upon actuation of one elongated implant member 20, 30, 40, 50, all four implant members 20, 30, 40, 50 rotate outwards, resulting in a second, expanded configuration as shown in FIG. 3b. This rotation is caused by the interaction of the gear teeth 23, 33, 43, 53 with each other. Hence, a rotation movement of one of said elongated implant members 20, 30, 40, 50 is transmitted by means of the gear teeth 23, 33, 43, 53 to the other elongated implant members 20, 30, 40, 50. In the second configuration the elongated implant members 20, 30, 40, 50 impart an X-shaped footprint to the expandable spinal implant 1.

The overall shape or footprint in said first and said second configuration may have multiple shapes. For instance, the footprint may be quadratic, oblong, circular or irregularly shaped. Furthermore, the elongated implant members 20, 30, 40, 50 may have a different lengths, for instance the first elongated implant member 20 and the second elongated implant members 30 may be longer than the third elongated implant member 40 and the fourth implant member 50.

Figure 4A:
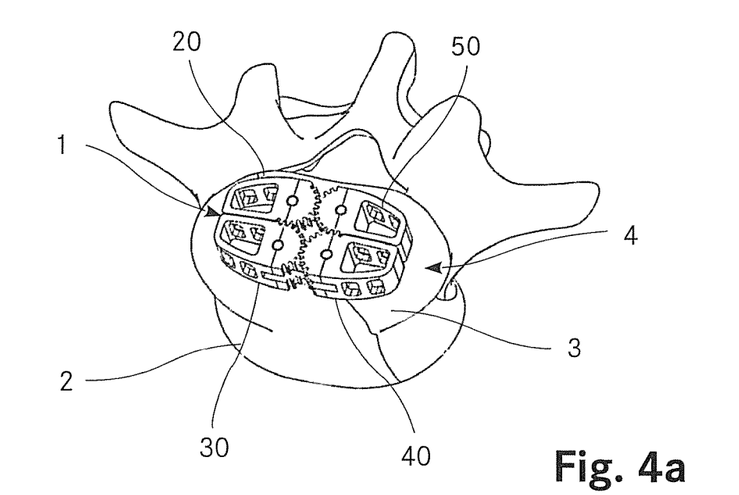
FIG. 4a, 4b the expandable spinal implant according to FIG. 1 arranged on a vertebral body.
Figure 4B:
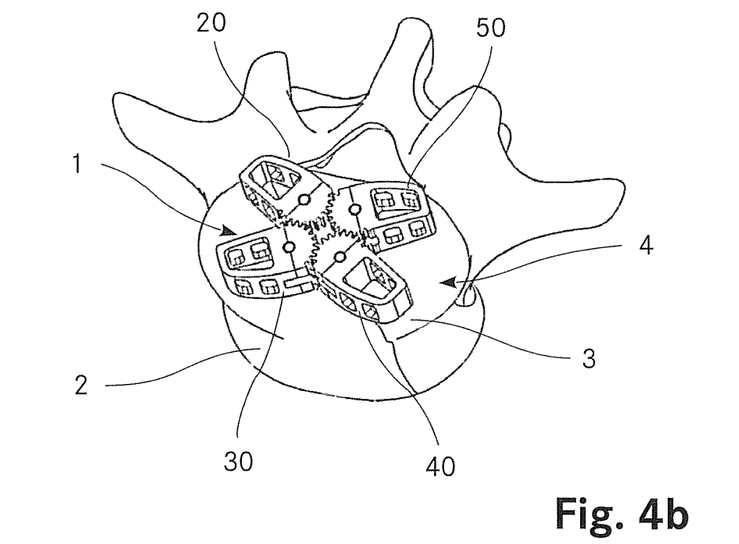

FIGS. 4a and 4b show the expandable spinal implant 1 arranged on a vertebral body 2. The expandable spinal implant 1 is thereby placed on the endplate 3 of the vertebral body 2 and occupies the intervertebral space 4 which would normally be occupied by the intervertebral disc. The adjacent vertebra on the other side of the intervertebral space 4 is not shown as it would cover the expandable spinal implant 1 in the perspective of the figure. FIG. 4a shows the expandable spinal implant 1 in the first, unexpanded configuration. In the second, expanded configuration, the elongated implant members 20, 30, 40, 50 are positioned close to the outer perimeter of the endplate 3 of the vertebral body 2, where the bone is denser, and withstands higher loads, as shown in FIG. 4b.

Figure 5A:
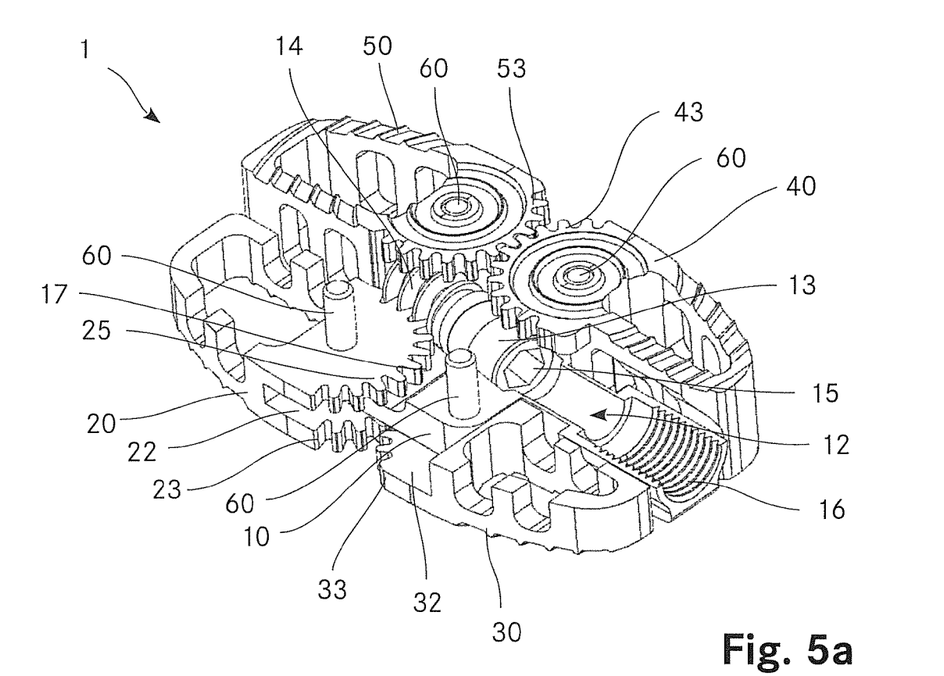
FIG. 5a-5c a second embodiment of an expandable spinal implant according to the present invention comprising a worm.
Figure 5B:
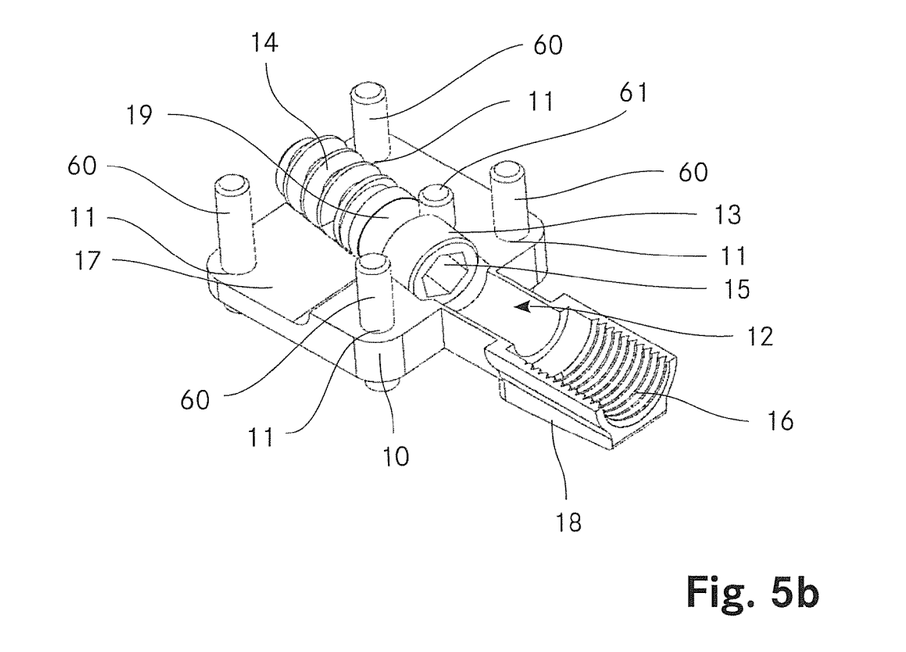
Figure 5C:
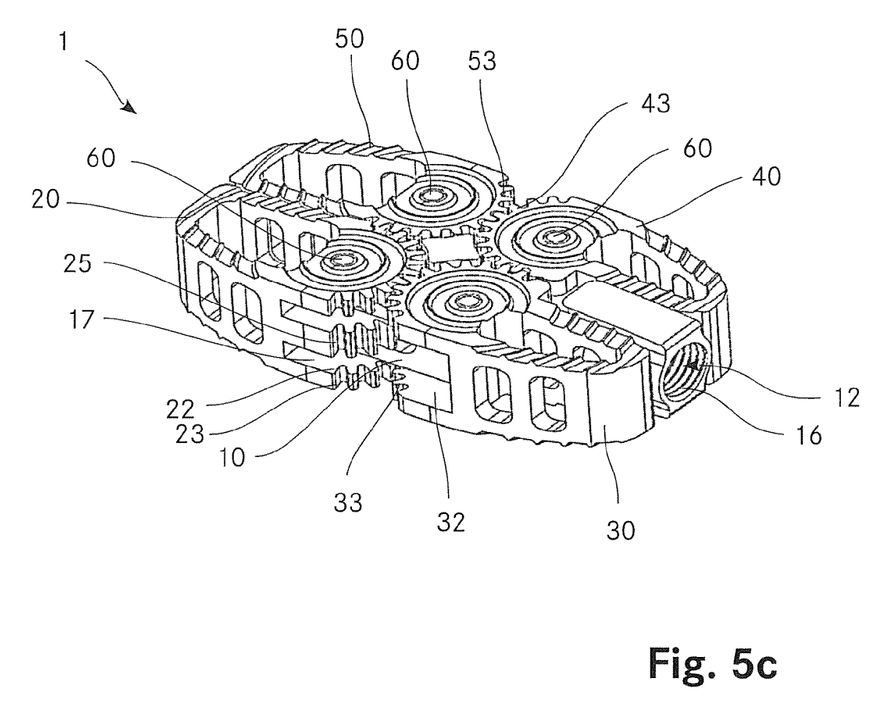

FIGS. 5a to 5c show a second embodiment of an inventive expandable spinal implant 1 according to the present invention. In FIG. 5a, the first elongated implant member 20 and the second elongated implant member 30 are shown in a cut-away view.

In this embodiment, the central base portion 10 comprises a channel 12 into which a worm 13 is arranged. The worm 13 includes a worm thread 14 which is in engagement with secondary gear teeth 25 of the first elongated implant member 20. Rotation of the worm 13 within the channel 12 will rotate the secondary gear teeth 25, as the worm thread 14 and the secondary gear teeth 25 constitute a worm-gear, and thus the first elongated implant member 20 will be rotated around the respective gear-pin 60. Such as to impart a rotation onto worm 13, a drive 15 is arranged on one end of said worm 13. Access to said drive 15 is made possible through the channel 12, e.g. for a suitable instrument. In the embodiment shown, the drive 15 is configured as hexagonal drive, however, other drive types may also be used, such as e.g. a torx-drive. The channel 12 includes an attachment portion 16 configured to be coupled to an insertion instrument. In the embodiment shown, the attachment portion 16 comprises a thread configured to cooperate with a matching thread of an insertion instrument (not shown). The secondary gear teeth 25 are arranged between the central base portion 10 and the first gear teeth 23. Such as to provide enough space for said secondary gear teeth 25, the central base portion 10 includes a groove 17.

FIG. 5b is a detailed view of the central base portion 10. The four hinge-pins 60 are shown inserted into their respective through-bores 11. As may be seen, the channel 12 extends further than the core of the central base portion 10 into a protrusion 18 which is sized and shaped such as to lie between the second elongated implant element 20 and the third elongated implant element 30 as shown in FIG. 5a. The worm 13 includes the worm thread 14 as well as a notch 19. The notch 19 cooperates with a peg 61 which protrudes from the central base portion 10. The cooperation of the notch 19 with the peg 61 keeps the worm 13 at the same position within the channel 12 while still allowing rotational movement of the worm 13. Further, the groove 17 is recognizable around the area of the hinge-pin 60 which will be coupled to the first elongated implant member 20.

FIG. 5c shows the second embodiment of an inventive expandable spinal implant 1 according to FIG. 5a in an overall view. All four elongated implant members 20, 30, 40, 50 are arranged generally parallel to each other, i.e. the expandable spinal implant 1 is in the un-expanded configuration. As may be seen on this picture, the first elongated implant member 20 comprises a set of secondary gear teeth 25 which cooperate with the worm thread (not shown in this picture).

Figure 6A:
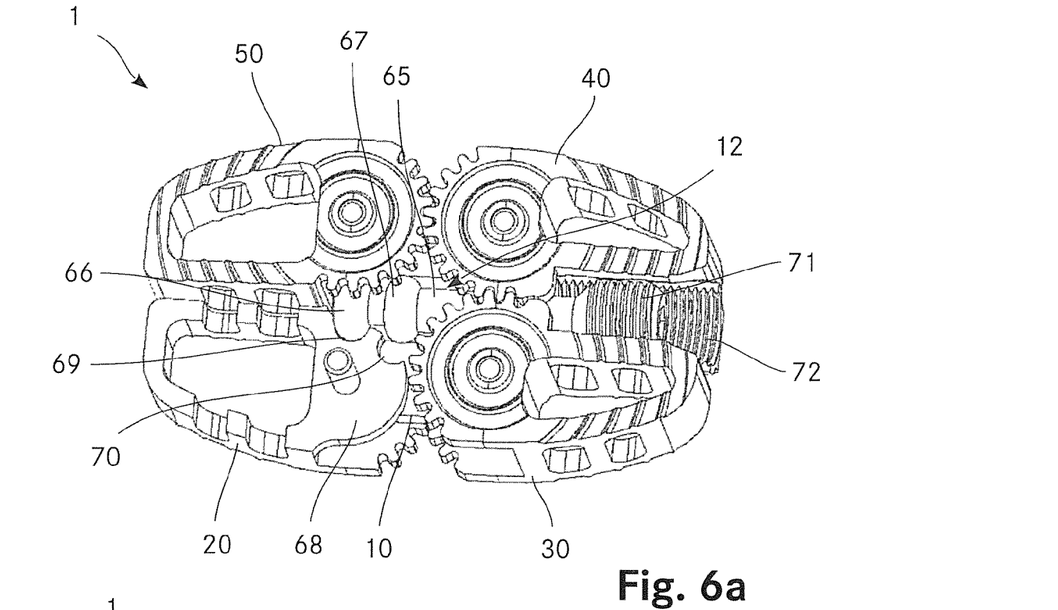
FIG. 6a, 6b a third embodiment of an expandable spinal implant according to the present invention comprising a dowel.
Figure 6B:
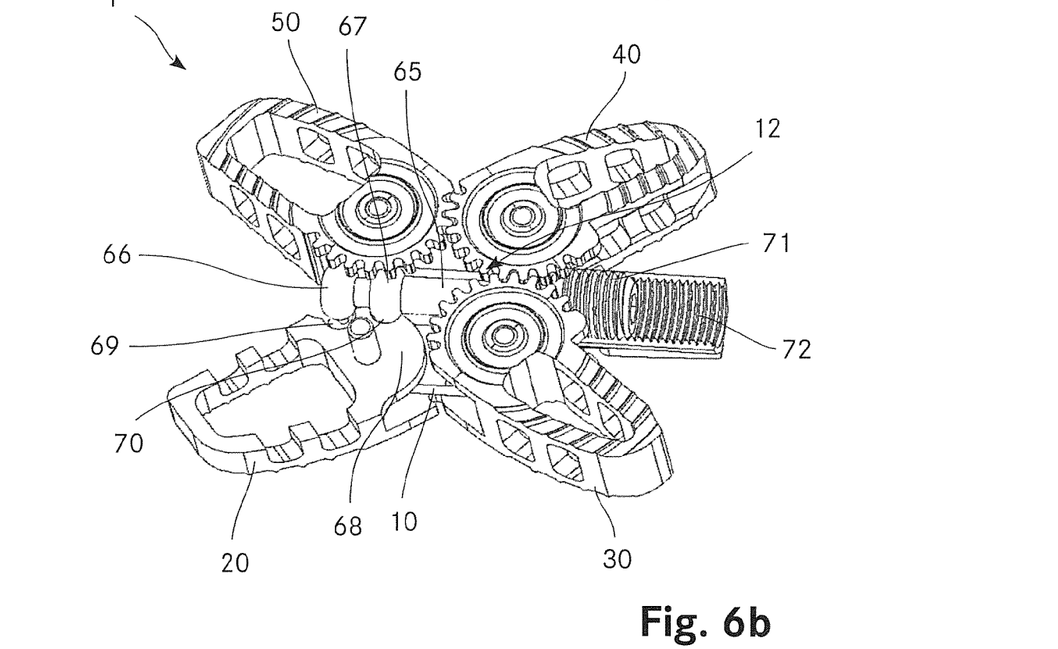

FIGS. 6a and 6b show a third embodiment of the expandable spinal implant 1 according to the present invention. In FIG. 6a, the first elongated implant member 20 is shown in a cut-away view. Compared to the embodiment as shown in FIGS. 5a and 5b, the present embodiment comprises a dowel 65 instead of a worm 13 arranged in the channel 12 of the central base portion 10. The dowel 65 may be linearly translated within the channel 12 and comprises a first structure including a first ring-like enlargement 66 and a second ring-like enlargement 67. Said first structure cooperates with a second structure arranged on a circular section 68 of the first elongated implant member 20. The second structure includes a first recess 69 and a second recess 70. In the first, un-expanded configuration of the expandable spinal implant 1 as shown in FIG. 6a, the first ring-like enlargement 66 is located within the first recess 69 in a form-fitting manner. Linear movement of the dowel 65 within the channel 12 will hence entail a rotational movement of the first elongated implant member 20 by means of the interaction of the first ring-like enlargement 66 with the first recess 69. Further, the peg 65 comprises a threaded head 71 with a drive. The threaded head 71 cooperates with an internal thread 72 located in said channel 12. By turning the dowel 65 via the drive, a linear translation of the dowel 65 will be mediated by the cooperation of the threaded head 71 with the internal thread 72.

FIG. 6b shows the third embodiment of the expandable spinal implant 1 in the second, expanded configuration. In this configuration, the dowel 65 is at a position within the channel 12 which is more towards said first elongated implant member 20 and said fourth elongated implant member 50 than in the first, un-expanded configuration shown in FIG. 6a. By the translational movement of the dowel 65, the first ring-like enlargement 66 pushed onto the first recess 69. This pushing force was translated in a rotational movement of the first elongated implant member 20. Mediated by the engagement of the gear teeth 23, 33, 43, 53 all of the elongated implant members 20, 30, 40, 50 are rotated. As the first ring-like enlargement 66 disengages from the first recess 69 after a certain distance of the translation of the dowel 65, and hence no further rotational movement of the four elongated implant members 20, 30, 40, 50 would be possible, the second recess 70 has been foreseen. Said second recess 70 is brought into form-fitting engagement with the second ring-like enlargement 67 of the dowel 65 after a predefined rotation of the first elongated implant member 20. This form-fitting engagement allows to impart further rotational movement to the first elongated implant member 20 by further linear movement of the dowel 65.

We claim:

1. An expandable spinal implant comprising three or more elongated implant members, said implant members rotatably coupled to a central base portion, wherein said implant members comprise a first end with an axis of rotation and circumferentially arranged gear teeth, wherein the gear teeth of at least one of said elongated implant members are interlocked into said gear teeth of the two other elongated implant members.

2. The expandable spinal implant of claim 1, wherein the elongated implant members are substantially parallel in an initial and unexpanded configuration.

3. The expandable spinal implant of claim 1, comprising four elongated implant members, wherein said four elongated implant members form a substantially X-shaped footprint in an expanded configuration.

4. The expandable spinal implant of claim 1, comprising three elongated implant members, wherein said three elongated implant members form a substantially Y-shaped footprint in an expanded configuration.

5. The expandable spinal implant of claim 1, comprising at least one pocket for receiving bone graft material.

6. The expandable spinal implant of claim 1, comprising elongated implant members of unequal length.

7. The expandable spinal implant of claim 1, comprising a worm arranged in said central base portion, said worm engaging a set of secondary gear teeth arranged on one of said elongated implant members.

8. The expandable spinal implant of claim 1, comprising a dowel having a first structure on one end, said first structure cooperating with a second structure on at least one of said elongated implant elements in a form-fitting manner, such as to rotate said one elongated implant member relative to said central base structure.

9. The expandable spinal implant according to claim 1, wherein the at least three elongated implant members each comprise a lower surface and an upper surface, said two surfaces being arranged at an angle to each other, said angle preferably being from 5° to 15°.

10. A kit comprising multiple expandable spinal implants of claim 1, wherein the expandable spinal implants have incremental thicknesses between 8 and 20 mm and/or elongated implant members with varying lengths and/or varying widths.

11. A kit according to claim 10, wherein the expandable spinal implants have varying angles between a lower surface and an upper surface of said at least three elongated implant members, said angles preferably varying from 5° to 15°.

* * * * *